US00PP34202P2

(12) United States Plant Patent
Hansen

(10) Patent No.: US PP34,202 P2
(45) Date of Patent: May 3, 2022

(54) ***ECHINACEA* PLANT NAMED 'TANAGER'**

(50) Latin Name: ***Echinacea* hybrid**
Varietal Denomination: Tanager

(71) Applicant: Hans A Hansen, Zeeland, MI (US)

(72) Inventor: Hans A Hansen, Zeeland, MI (US)

(73) Assignee: Walters Gardens Inc., Zeeland, MI (US)

( * ) Notice: Subject to any disclaimer, the term of this patent is extended or adjusted under 35 U.S.C. 154(b) by 0 days.

(21) Appl. No.: 17/300,435

(22) Filed: Jun. 29, 2021

(51) Int. Cl.
*A01H 5/02* (2018.01)
*A01H 6/14* (2018.01)

(52) U.S. Cl.
USPC ..... Plt./428
CPC ..... *A01H 6/1448* (2018.05)

(58) Field of Classification Search
USPC ..... Plt./428
CPC ..... A01H 5/02
See application file for complete search history.

*Primary Examiner* — Kent L Bell

(57) ABSTRACT

The new and distinct cultivar of *Echinacea* plant named 'Tanager' with fragrant inflorescences on strong, dark, branched stems producing single whorls of rich tangerine-orange ray florets. The large inflorescence produces ray florets that tend to stay nearly horizontal through maturity. The cones on the new plant are dark wine-colored. The new plant flowers from mid-summer to late summer, and is suitable as a potted plant, for the landscape, and for cut flower arrangements.

1 Drawing Sheet

Botanical denomination: *Echinacea* hybrid.
Cultivar designation: 'Tanager'.

STATEMENT REGARDING PRIOR DISCLOSURES UNDER 37 CFR 1.77(B)(6)

The first non-enabling disclosures of the claimed plant, in the form of a photograph and brief description on a website operated by Walters Gardens, Inc. on Feb. 1, 2020 followed by a photograph and brief description in the "Walters Gardens 2020-2021 Catalog" on May 20, 2020. The claimed plant was first sold on Jun. 29, 2020 by Walters Gardens, Inc., who obtained the plant and all information relating thereto, from the inventor. No plants of *Echinacea* 'Tanager' have been sold in this country or anywhere in the world, nor has any disclosure of the new plant been made, more than one year prior to the filing date of this application, and such sale or disclosure within one year was either derived directly or indirectly from the inventor.

BACKGROUND OF THE INVENTION

The present invention relates to the new and distinct cultivar of Coneflower from the genus *Echinacea* and given the cultivar name 'Tanager'. The new plant was the result of a cross by the inventor of an unnamed proprietary hybrid known as 15-27-8 (not patented) as the female parent and an unnamed proprietary hybrid known as 15-27-7 (not patented) as the male on Aug. 8, 2015 at a wholesale perennial nursery in Zeeland, Mich. The single seedling selected was evaluated first in trials in the summer of 2017 at the same nursery and assigned the breeder code of 16-52-1.

*Echinacea* 'Tanager' has been asexually propagated at the same nursery by crown division since 2018 and also using careful shoot tip tissue culture procedures and found to reproduce plants that exhibit all the characteristics identical to the original plant in successive generations.

*Echinacea* 'Tanager' is distinct from all other Coneflowers known to the inventor. The nearest comparison cultivars are: 'Frankly Scarlet' U.S. Plant Pat. No. 33,582 'Balsomador' U.S. Plant Pat. No. 26,639, 'Julia' U.S. Plant Pat. No. 24,629, 'Flame Thrower' U.S. Plant Pat. No. 21,932, 'Tiki Torch' U.S. Plant Pat. No. 18,839, 'TNECHKIO' U.S. Plant Pat. No. 28,769, 'Tomato Soup' U.S. Plant Pat. No. 19,427 and 'Orange You Awesome' U.S. Plant Pat. No. 32,105.

The female parent plant, 15-27-8, was not maintained as either plants or in photography, so no comparison is possible. The male parent plant, 15-27-7, was not maintained as either plants or in photography, so no comparison is possible.

'Frankly Scarlet' is slightly taller in habit and the ray florets are more intense bright scarlet-orange. 'Balsomador' is slightly smaller in habit and ray florets have a more reddish-orange overlay and droop more in maturity, and the cone color is lighter. 'Julia' has narrower ray florets that are less overlapping, droop more in maturity and more greyed-orange to reddish-orange on taller plants. 'Flame Thrower' produces much taller and broader plants with ray florets that cup down producing duller ray florets with more greyed orange to orangish-yellow. 'Tiki Torch' is much taller in habit, the inflorescences are smaller and the ray florets are orangish-pink. 'TNECHKIO' has much shorter habit, smaller inflorescences and the ray florets are more reddish-orange. 'Tomato Soup' has florets that droop more and are not as overlapping, and the habit is nearly twice as tall as the new plant. 'Orange You Awesome' is slightly shorter and has ray florets that are less overlapping of a lighter tangerine orange color.

SUMMARY OF THE INVENTION

*Echinacea* 'Tanager' has not been evaluated under all possible environmental conditions. The phenotype may vary with variations in environment including: growing temperature, available sunlight, nutrients, water, etc. without a change in the genotype of the plant. The new plant is distinct from its parents and all other *Echinacea* known to the applicant in the following combined traits:

1. Fragrant inflorescences on strong branched stems;
2. Large, broad inflorescences with single whorl of ray florets that tend to stay horizontal once open;
3. Ray florets of rich tangerine-orange with dark stems and dark wine-colored cones;
4. Vigorous growth and excellent habit;
5. Dark-green ovate foliage.

BRIEF DESCRIPTION OF THE DRAWINGS

The photographs of 'Tanager' demonstrate the overall appearance of the plant including the unique traits. The drawings of the new plant are of a two-year-old plant grown in full-sun trial garden in Zeeland, Mich. The colors are as accurate as reasonably possible with color reproductions. Some slight variation of color may occur as a result of lighting quality, intensity, wavelength, direction or reflection.

DETAILED DESCRIPTION OF THE PLANT

Figure 1:
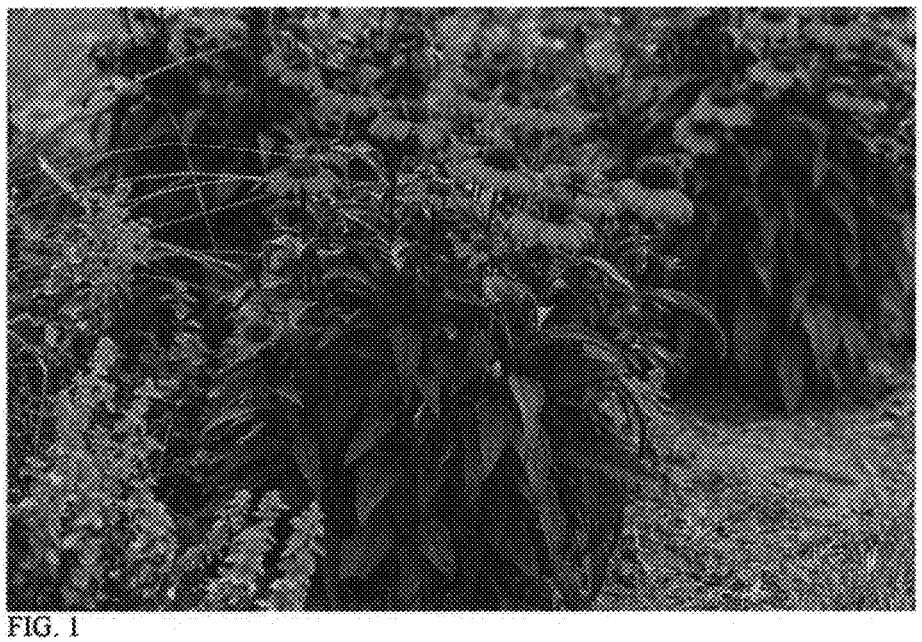
FIG. 1 shows the habit of the new plant in flower.
Figure 2:
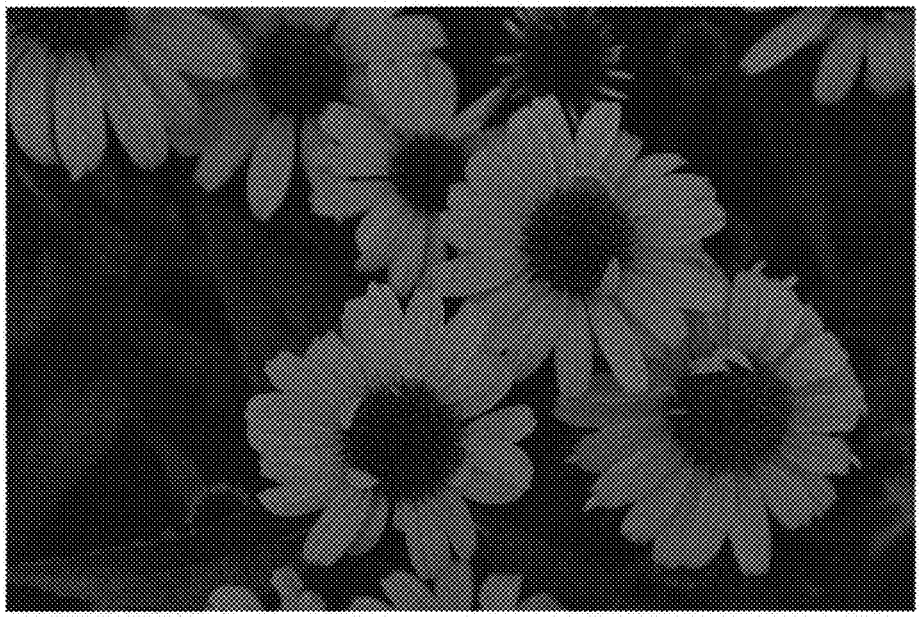
FIG. 2 shows a close up of some inflorescences from above.

The following description of *Echinacea* 'Tanager' is based on observations of two-year-old specimens grown in a partially shaded greenhouse in Zeeland, Mich. The new plant has not been tested in all environments and some phenotypic differences may occur with different environments without, however, any change in genotype. The color descriptions are based on the 2015 edition of The Royal Horticultural Society Colour Chart except where common dictionary descriptions are used.

Parentage: Female or seed parent is the proprietary unreleased hybrid 15-27-8 and male parent is the proprietary unreleased hybrid 15-27-7 comprising of 'Little Annie' (not patented) and 'Solar Flare' U.S. Plant Pat. No. 20,133;

Plant habit: Multi-stemmed, freely-branched, hardy herbaceous perennial, flowering to about 45 cm tall and foliage to 25 cm tall and 34 cm wide;

Growth rate: Vigorous, finishing in 4 liter containers in about 2 months during the summer;

Roots: Cream-colored, finely branched;

Foliage: Alternate; ovate; acute apex; attenuate base; margin dentate, micro-ciliolate; hirsutulous abaxial and adaxial; to about 14.0 cm long and 6.0 cm wide decreasing distally, average about 12.5 cm long and 4.2 cm wide;

Leaf color: Young leaves adaxial nearest RHS 137B, abaxial nearest RHS 137C; mature leaves adaxial nearest NN137A, abaxial nearest RHS 137B;

Foliage fragrance: Lightly herbal;

Venation: Pinnate; with two major arcuate veins on both sides of the midrib; abaxial midrib and veins costate; glabrous adaxial, hirsutulous abaxial;

Vein color: Adaxial midrib and primary veins nearest RHS 193A, secondary nearest RHS NN137A; abaxial primary veins between RHS 146D and RES N144A, secondary nearest RHS 137A;

Petiole: Concavo-convex, strigillose adaxial and sparsely puberalent to strigillose abaxial; to about 17 cm long and 1.0 mm wide at the base on lowest leaves and decreasing to nearly sessile distally; color nearest adaxial nearest 137A, abaxial nearest RHS 137B with adaxial midrib between RHS 146D and RHS 145C and abaxial midrib nearest RHS 146D;

Peduncle: Strigillose; cylindrical; strong stiff; average 35 cm long and 8.0 mm diameter at base; quantity per plant about seven;

Peduncle color: Nearest RHS 146C proximally with a strong blush to solid nearest RHS 187C distally;

Internode: About 12 per peduncle; average about 2.9 cm long, shorter proximally and longer distally; node color same as surrounding peduncle;

Branches: Cylindrical, strigillose; tightly angled to main stem to about 60° above horizontal: to about 20 cm long and 4.5 mm diameter; color nearest RHS 146C proximally with a strong blush to solid nearest RHS 187C distally;

Inflorescence: Bracteate head, aggregate of achene; with single whorl of distinct ligulate ray florets and disk florets in a pappus; flowering mid-summer to late summer; initial inflorescence largest, to about 10 cm wide and 4.8 cm tall, average about 8.0 cm diameter, with cones 4.0 cm across and 4.5 cm tall; approximately 4 inflorescences per peduncle;

Inflorescence fragrance: Lightly sweet;

Flower persistence: Remaining effective in color for 10 to 14 days depending on temperatures, cone drying on plant and effective into winter;

Involucre: With numerous bracts, about 65 per inflorescence in 4 to 5 whorls; arcuate downward toward peduncle;

Involucre bracts: Lanceolate to linear; narrowly acute apex; truncate base; micro-ciliolate margin; adaxial glabrous to micro-puberulent; abaxial strigillose; to about 13.0 mm long and 5.0 mm across decreasing distally; color nearest RHS 147C adaxial center, abaxial center nearest RHS 138B, adaxial margin nearest RHS 139A and abaxial margins nearest RHS 137B;

Inflorescence buds with ray florets vertical and still enrolled: About 22 mm across and 22 mm tall; ray floret color nearest RHS N77B with spines nearest RHS 187A;

Ray florets: Zygomorphic; arrangement in single whorl, frequently lightly imbricate; ligulate, apex emarginated with two or more notches to 3.0 mm deep; base attenuate; margin entire; adaxial and abaxial surfaces matte; 18 to 24 per inflorescence; opening to horizontal, drooping up to only 15 degrees below horizontal with maturity; astemonous; ray floret to 44.0 mm long and 11.0 mm wide, average size 32.0 mm long, 8.5 mm wide at center tapering to 2 mm wide at base; thickened veins raised adaxial;

Ray floret color: Changing with maturity; when first horizontal young adaxial nearest RHS 169A with basal 2 mm nearest RHS 184C; abaxial young nearest RHS 186D with veins nearest RHS 186B, basal 2 mm between RHS 146D and RHS N144A; mature adaxial distal and center portions between RHS 168D, RHS 173D and RHS N170C, proximally between RHS 71B and RHS 173D with base nearest RHS 146D; mature abaxial nearest RHS 159C with veins lighter than RHS 186D;

Disk florets: About 250 to 400 per head; actinomorphic; perfect; synandrous; produced in raised dome, about 4.5 cm across and 4.0 cm tall;

*Disk floret corolla*.—Fused forming tube; about 5.0 mm long and 2.0 mm wide, fused in tube in basal 4.0 mm, free in distal 1.0 mm; individual disk florets about 0.5 mm wide at fusion; acute apex; entire margin; both surfaces slightly lustrous.

*Disk floret corolla tube color*.—Adaxial and abaxial nearest RHS 146D, except distal 0.5 mm nearest RHS 183C.

*Disk floret androecium*.—Five; synandrous.

*Androecium*.—Present on disk florets only.

*Staminal column*.—About 0.7 mm wide and protrudes from corolla tube about 2 mm; five fused stamens; color nearest RHS 200A.

*Anthers*.—Fused, about 3.0 mm long and 0.7 mm diameter; color nearest RHS 200A.

*Filaments*.—Five; attached to column; thin, less than 0.2 mm diameter and 0.5 mm long; color nearest RHS 158D.

*Pollen*.—Globose, less 0.1 mm in diameter; color nearest RHS 17A.

*Gynoecium*.—Single; to 9.0 mm long; present on both ray and disk florets.

*Style*.—About 4.0 mm long and 0.3 mm diameter; color nearest RHS 200A.

*Stigma*.—Bifid; about 1.5 mm long and 0.3 mm diameter; color nearest RHS N186A.

*Fruit*.—Achene; pyramidal; about 4 mm long and 3 mm wide; acute base and fringed flattened apex; color variable nearest RHS 199D and between RHS 202A and RHS 202B.

Receptacle spines: With disk florets; acicular; lustrous; to 14 mm long and 1.5 mm across;

Spine color: Upon opening apices nearest RHS 187A, center portion nearest 138A with bases nearest RHS 145C; mature flower apices nearest RHS N186C, central portion nearest RHS 138A, and base nearest RHS 145D; after ray florets fall apices nearest RHS 178A, midsection nearest RHS 138A with base nearest RHS 145D; after dried base nearest RHS N200A and distal 5.0 mm nearest RHS 202A;

Disease resistance: Resistance and susceptibility beyond that of other hardy Coneflower cultivars has not been observed.

Growth: The plant grows best with plenty of moisture and adequate drainage, but is able to tolerate some drought when mature.

Hardiness: at least from USDA zone 4 through 8.

I claim:

1. A new and distinct cultivar of *Echinacea* plant named 'Tanager' as herein described and illustrated.

* * * * *